US006991793B2

(12) United States Patent　(10) Patent No.: US 6,991,793 B2
Shoemaker et al.　(45) Date of Patent: Jan. 31, 2006

(54) **METHOD OF PROTECTING FISH AGAINST COLUMNARIS DISEASE WITH MODIFIED LIVE *FLAVOBACTERIUM COLUMNARE***

(75) Inventors: Craig A. Shoemaker, Notasulga, AL (US); Phillip H. Klesius, Auburn, AL (US); Joyce J. Evans, Chestertown, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/870,781

(22) Filed: Jun. 17, 2004

(65) Prior Publication Data

US 2004/0234535 A1　Nov. 25, 2004

Related U.S. Application Data

(62) Division of application No. 10/020,735, filed on Dec. 12, 2001, now Pat. No. 6,881,412.

(51) Int. Cl.
*A61K 39/00* (2006.01)
*A61K 39/02* (2006.01)
*C12N 1/00* (2006.01)

(52) U.S. Cl. .................... 424/184.1; 435/317.1; 424/234.1; 424/252.1

(58) Field of Classification Search ........... 424/184.1, 424/234.1, 199.1, 252.1; 435/69, 850, 317.1, 435/234.1, 252.1
See application file for complete search history.

(56) References Cited

U.S. PATENT DOCUMENTS 5,284,653 A * 2/1994 Wolf-Watz et al. ...... 435/252.1

OTHER PUBLICATIONS

Bader, J. et al, Comparison of whole-cell antigens of pressure and formalin-killed *Flexibacter columnaris* from channel catfish (Ictalurus punctatus, Am J Vet Res, 1997; 58(9): 985-988.*
Klesius, P. et al, Effect of feed deprivation on innate resistance and antibody response to *Flavobacterium columnare* in channel catfish, Ictalurus punctatus, Bulletin European Association of Fish Pathologist, 1999; 19(4): 156-8.*
Decostere, S. et al, Shieh medium supplemented with tobramycin for selective isolation of *Flavobacterium columnare* (*Flexibacter columnaris*) from diseased fish, Journal of Clinical Microbiology, 1997; 35(1): 322-24.*

* cited by examiner

*Primary Examiner*—Lynette R. F. Smith
*Assistant Examiner*—Lakia J. Tongue
(74) *Attorney, Agent, or Firm*—John D. Fado; Curtis P. Ribando; Lesley Shaw

(57) ABSTRACT

Safe and effective live vaccines against *Flavobacterium columnare* of fish were created through the induction of rifampicin resistance in a native *Flavobacterium columnare* isolate; these including rifampicin-resistant mutants NRRL B-30303 and B-30304. Single immersion exposure of fish stimulated acquired immunity against virulent *F. columnare* infection.

6 Claims, No Drawings

METHOD OF PROTECTING FISH AGAINST COLUMNARIS DISEASE WITH MODIFIED LIVE *FLAVOBACTERIUM COLUMNARE*

CROSS REFERENCE TO RELATED APPLICATIONS

This application is a divisional of application Ser. No. 10/020,735, filed on Dec. 12, 2001, now U.S. Pat. No. 6,881,412, the contents of which are herein incorporated by reference.

BACKGROUND OF THE INVENTION

1. Field of the Invention

*Flavobacterium columnare* is an aquatic bacterium that is highly infectious in both warm and cold water species of fish. In the channel catfish (*Ictalurus punctatus*), it is the causative agent of columnaris disease. *Flavobacterium columnare* is a Gram-negative, rod shaped, pathogen that has been isolated from channel catfish in areas of the southeastern United States where this species is cultured. The disease also affects sports fish (i.e., walleye and largemouth bass) and aquarium fishes. Medicated feed (antibiotics) is currently used to try and control this bacterial infection. However, these treatments are limited in their effectiveness and most producers have discontinued use of medicated feeds. Prevention of columnaris disease by vaccination is an important goal and a top priority of catfish and other fish producers throughout the world. Estimated savings to these industries would be in excess of $100 million annually.

This invention relates to a novel vaccine against columnaris which does in fact provide superior protection over commercial treatment involving treating the water with potassium permanganate ($KMnO_4$) or feeding medicated feeds.

2. Description of the Prior Art

It has been estimated that columnaris is the second leading cause of mortality in pond raised catfish in the southeastern United States. Based on the success of disease control by immunization with killed bacteria (i.e., bacterins) in salmonids, experimental bacterins have been developed and tested against *F. columnare*. However, no vaccine is currently available and vaccination is not practiced in the catfish industry against *F. columnare*, presumably because the inactivation (i.e., formalin treatment) destroys the antigen (Bader et al., Comparison of whole-cell antigens of pressure- and formalin-killed *Flexibacter columnaris* from channel catfish (*Ictalurus punctatus*), American Journal of Veterinary Research, 58, pg. 985–988, 1997). The patent of Wolf-Watz et al. (U.S. Pat. No. 5,284,653) presents a list of bacteria, one of which is *Flexibacter columnaris* (now *F. columnare*) which has the potential to be genetically modified to produce a vaccine. However, no data are presented on *F. columnare* vaccines, only on genetically modified mutant vaccines of *Vibrio anguillarum*. Bernadet (Immunization with bacterial antigens: *Flavobacterium* and *Flexibacter* infections, Fish Vaccinology: Developments in Biological Standardization, Volume 90, pg. 335–340, 1997; Karger Switzerland: Basel) reviews the limited knowledge available on *F. columnare* and vaccination against this important disease. Work suggests that rainbow trout (*Oncorhynchus mykiss*) which survive infection with *F. columnare* are immune to subsequent disease.

SUMMARY OF THE INVENTION

We have now discovered a means for the creation of novel live vaccines that are safe and effective for the control of *F. columnare* in catfish. The vaccines comprise one or more rifampicin (3-[4-methylpiperazinyl-iminomethyl]rifamycin SV) (Sigma Chemical Company, St. Louis, Mo.) resistant mutants of *F. columnare*, created by multiple passaging of the native isolate on increasing concentrations of rifampicin. These vaccines are effective in providing long lasting acquired immunity in channel catfish to *F. columnare*.

In accordance with this discovery, it is an object of the invention to provide a novel, highly protective, live vaccine against *F. columnare* in fish, such as eels (*Anguilla* sp.), salmonids (*Oncorhynchus* sp. and *salmo* sp.), tilapia (*Oreochromis* sp.), hybrid-striped bass (*Morone chrysops* x *M. saxatilis*), walleye (*Stitzostedion vitreum*), channel catfish, cetrachids (such as largemouth bass (*Micropterus salmoides*)),. bait minnows (*Pimephales promelas*), goldfish (*Carassius auratus*), carp (*Cyprinus carplo*), and aquarium fish (tropical fish species such as black mollies (*Poecilia sphenops*)) and platies (*Xiphophorus maculatus*).

It is another object to provide an attenuated *F. columnare* vaccine that is safe and provides long lasting acquired immunity in fish to columnaris disease, including channel catfish.

It is a further object of this invention to improve the viability and productivity of catfish, and to reduce economic losses in the fish industry caused by columnaris disease.

Other objects and advantages of the invention will become readily apparent from the ensuing description.

Deposit of Biological Material

Two rifampicin-resistant attenuated *F. columnare* isolates, were deposited on Jun. 20, 2000 under the provisions of the Budapest Treaty in the Agricultural Research Service Culture Collection in Peoria, IL, and have been assigned Deposit Numbers NRRL B-30303 and NRRL B-30304.

DETAILED DESCRIPTION OF THE INVENTION

"Vaccine" is defined herein in its broad sense to refer to any type of biological agent in an administrable form capable of stimulating a protective immune response in an animal inoculated with the vaccine. For purposes of this invention, the vaccine may comprise one or more live attenuated mutants of *F. columnare* having the characteristic of rifampicin-resistance.

The starting material for use in preparing the vaccines of the invention is any attenuated *F. columnare* bacterium such as those reported, supra. Serial passage of the isolate of *F. columnare* over increasing concentrations of rifampicin produces strains with an attenuated pathogenicity efficacious for the preparation of live vaccines. The attenuation achieved by high-level serial passage in culture on increasing concentrations of rifampicin virtually eliminates the pathogenicity of the bacterium toward fish. The native strain of *F. columnare* should be passaged a sufficient number of times such that in its new attenuated form it no longer possesses the ability of causing the disease state known as columnaris in catfish. The methodology for attenuation by serial passage is well known and documented in the art as exemplified by Schurig et al. [*Vet. Micro.* 28, 171–188 (1991)], hereby incorporated by reference, who created vaccines based on modified live rifampicin-resistant *Brucella* species.

Vaccination, while being accomplishable by injection or through oral ingestion, is most efficiently done by means of aqueous immersion. The bacterial agent is prepared for administration by formulation in an effective immunization dosage with an acceptable carrier or diluent, such as water. The expression "effective immunization dosage" is defined as being that amount which will induce immunity in a fish against challenge by a virulent strain of *Flavobacterium columnare*. Immunity is considered as having been induced in a population of fish when the level of protection for the population is significantly higher than that of an unvaccinated control group. One measure of protection following experimental challenge is relative percent survival (RPS) as described by Amend (1981; Dev. Biol. Stand., 49, 447–454), herein incorporated by reference. RPS is calculated according to the following formula:

$$RPS = 1 - \frac{\% \text{ vaccinate mortality}}{\% \text{ control mortality}} \times 100$$

A positive vaccinal effect is indicated by a RPS equal to or greater than 60%. Typically, vaccination is carried out by exposing fish by immersion in water containing about $1 \times 10^6$ CFU/ml of attenuated *Flavobacterium columnare* for 15 minutes at a density of about 50 fish/L and a temperature of about 25° C. CFU denotes colony forming units of *F. columnare*. These parameters may be varied as desired such that a sufficient level of vaccination is acquired without induction of stressful conditions or loss of fish. Useable concentrations of *Flavobacterium columnare* are considered to range from about $5 \times 10^5$ to about $1 \times 10^8$ CFU/ml of immersion medium. Useable vaccination times are seen to range from about 1 minute to about 60 minutes, preferably from about 2 minutes to about 15 minutes. Temperature of the inoculation media may range within the physiologically acceptable limits of the fish involved, for channel catfish preferably from about 18° C. to about 28°, most preferably from about 22° C. to about 26° C. Concentrations of fish treated in the inoculation medium typically range from about 50 to about 100 fish/L, but, in the alternative, may be determined on a weight basis and range from about 0.5 to about 2.5 kg/L. The vaccine can be effectively administered any time after the fish attains immunocompetence, which for channel catfish is at about two to fourteen days post-hatch. Other species of fish susceptible to *F. columnare* can be immunized after 21–30 days post-hatch or when they become immunocompetent to modified live vaccine administered by immersion.

Appropriate adjuvants as known in the art may also be included in the vaccine formulation.

The following examples are intended only to further illustrate the invention and are not intended to limit the scope of the invention which is defined by the claims.

EXAMPLE 1

The procedure used to produce the *F. columnare* vaccine mutants was modified from that described in Shurig et al. (1991; Vet Micro, 28, 171–188), hereby incorporated by reference, by using a lower initial concentration of rifampicin and ending at 200 µg/ml after 243 passages instead of 51 passages and by omitting the penicillin step.

Process of Developing Resistant Mutants of *Flavobacterium columnare*

Modified *Cytophaga* agar plates for the cultivation of *Flavobacterium columnare* were made according to the procedure of Klesius et al. (Effect of feed deprivation on innate resistance and antibody response to *Flavobacterium columnare* in channel catfish, *Ictalurus punctatus*. Bulletin European Association of Fish Pathologists, 19(4), 156–158, 1999). 1.0 g tryptone, 0.5 g yeast extract, 0.2 g beef extract, 0.2 g sodium acetate and 9.0 g of agar were added to one liter of distilled water. The medium was heated until dissolution. The medium was then autoclaved at 121–124° C. for 15 minutes, poured into sterile petri dishes (15 ml per dish) and allowed to solidify before refrigeration.

Native isolates of *Flavobacterium columnare* were obtained from sick catfish or previously obtained lyophilized stocks. Isolates of *F. columnare* were then identified by standard biochemical tests as set forth in *Bergey's Manual of Determinative Bacteriology* prior to use in rifampicin resistant *F. columnare*. After identification, the process of forming rifampicin resistant isolates of F. columnare was begun. Rifampicin supplemented modified *Cytophaga* agar plates were prepared as follows: Modified *Cytophaga* agar was made as described above and sterilized at 121–124° C. for 15 minutes. After sterilization, the correct amount of rifampicin was added to the media prior to its solidification and 15 ml of the resulting mixture was poured into separate petri dishes and allowed to solidify prior to refrigerated storage. Initial cultures of the native isolates of *F. columnare* were grown on modified *Cytophaga* agar plates which were incubated at 20–25° C. for 24–48 hours or until 1–2 mm yellow, rhizoid colonies were observed. A single *F. columnare* colony was then picked with a sterile inoculating loop and streaked onto a rifampicin supplemented modified *Cytophaga* agar plate containing the correct concentration of the antibiotic. For the initial passage, rifampicin was present in the modified *Cytophaga* agar at a concentration of 5 µg/ml. The rifampicin-supplemented modified *Cytophaga* agar which was streaked with the aforementioned native isolate of *F. columnare* was then incubated for 24–48 hours at 20–250° C. and observed for bacterial growth. Single colonies of *F. columnare* which grew on the rifampicin-supplemented medium were then picked and placed onto the next concentration of rifampicin (10 µg/ml) modified *Cytophaga* agar plates. If growth occurred, a single colony was harvested and placed on an agar medium containing the next higher concentration of rifampicin (20 µg/ml). If the harvested colony failed to grow, it was repeatedly passed on a medium containing the last concentration of rifampicin at which growth successfully occurred, before being placed on the next higher concentration of rifampicin-containing medium. This process was repeated until a colony capable of growing on a medium containing a rifampicin concentration of 200 µg/ml was created.

*Flavobacterium columnare* isolate ARS-1 was passaged on increasing concentrations of rifampicin (Sigma Chemical Company, St. Louis, Mo.) supplemented modified *Cytophaga* agar to a final concentration of 200 µg/ml rifampicin for 243 passages. The resultant mutants (i.e., two colonies from the original passage that grew and were passaged), designated NRRL B-30303 and NRRL B-30304, are differentiated from the parent microorganism because they can survive and reproduce on a media containing 200 µg/ml rifampicin without negative effect. Biochemical characteristics of the *F. columnare* B-30303 and B-30304 are identical to *F. columnare* as described in *Bergey's Manual of Determinative Bacteriology* (Holt et al., 1994), herein incorporated by reference.

EXAMPLE 2

Safety and Back-Passage

The safety and back-passage study revealed both vaccine candidate rifampicin mutants were safe for use in vaccination of 10 day post hatch channel catfish at concentrations of $1.4 \times 10^8$ or $6.7 \times 10^7$ CFU/ml for a 30 minute immersion exposure. One hundred and twenty five fish were used for each group which included the initial exposure and then each subsequent exposure for a total of 5 passages (i.e., fish to fish transfer). One hundred channel catfish not exposed to *F. columnare* mutants were kept as negative controls. The numbers of fish which died after exposure to the vaccine or vaccine diluent (i.e., controls) are presented in Table 1. Forty eight hours following exposure, 40 fish were removed, homogenized and cultured for the presence of *F. columnare* vaccine strains at each passage and in the control group. The vaccine isolates were isolated at the first passage but not at subsequent passages indicating that the vaccine strains were capable of invading the fish, but did not revert to virulence following back-passage and thus, were attenuated in 10 day post hatch channel catfish. The fish used in this experiment were held in the laboratory without signs of columnaris disease or adverse behavior for at least 21 days following treatment.

TABLE 1

SAFETY OF VACCINE DOSE OF *F. COLUMNARE* MUTANTS IN 10 DAY POST HATCH CHANNEL CATFISH VACCINATES

| Mutant | Passage | No. Dead/ No. Total[1] | *F. columnare* Mutant Isolated from homogenized fish | Percent Mortality |
|---|---|---|---|---|
| B-30303 | 1 | 14[2]/125 | Yes | 11.2 |
| | 2 | 0/125 | No | 0.0 |
| | 3 | 0/125 | No | 0.0 |
| | 4 | 0/125 | No | 0.0 |
| | 5 | 0/125 | No | 0.0 |
| B-30304 | 1 | 17[3]/125 | Yes | 13.6 |
| | 2 | 1[4]/125 | No | 8.0 |
| | 3 | 12[5]/125 | No | 9.6 |
| | 4 | 2[6]/125 | No | 1.6 |
| | 5 | 0/125 | No | 0.0 |
| Controls | None | 13[7]/100 | No | 13.0 |

[1]Note, total number of fish to start the experiment was used for calculations.
[2]1 of 14 positive for rifampicin resistant *F. columnare*.
[3]1 of 17 positive for rifampicin resistant *F. columnare*.
[4]*F. columnare* not isolated from dead fish.
[5]*F. columnare* not isolated from dead fish.
[6]*F. columnare* not isolated from dead fish.
[7]*F. columnare* not isolated from dead fish.

EXAMPLE 3

Efficacy

Channel catfish (125, USDA 103 strain) were vaccinated by adding 40 ml of *F. columnare* mutant B-30303 to 7.5 L of water for a 30 minute exposure. One-hundred twenty five USDA 103 channel catfish were exposed by adding 40 ml of vaccine diluent to 7.5 L of water for a 30 minute exposure to serve as control fish (i.e., non-vaccinated). Vaccinated and control fish were held for 32 days following vaccination before they were challenged with virulent *F. columnare*. No fish died after the vaccination. Results of experimental challenge are presented as relative percent survival (RPS) as described by Amend (1981; Dev. Biol. Stand., 49, 447–454), herein incorporated by reference. RPS is calculated according to the following formula:

$$RPS = 1 - \frac{\%\text{ vaccinate mortality}}{\%\text{ control mortality}} \times 100$$

A positive effect by vaccination is a RPS greater than 50%. At fourteen days post vaccination (DPV), the relative percent survival (RPS) was 69.2%. In this study, mortality in an equivalent group of 125 untreated controls was 20.8% versus 6.4% mortality in the 125 vaccinated fish.

TABLE 2

PROTECTION AGAINST COLUMNARIS DISEASE AFTER IMMERSION VACCINATION[1] OF CHANNEL CATFISH WITH *FLAVOBACTERIUM COLUMNARE* B-30303 VACCINE

| Treatment | No. Dead/ No. Total | Percent Mortality | Relative Percent Survival (RPS)[2] |
|---|---|---|---|
| Vaccinated with B-30303 | 8/125 | 6.4 | 69.2 |
| Control (non-vaccinated) | 26/125 | 20.8 | — |

[1]Immersion vaccination for 30 minutes with $5 \times 10^6$ CFU/ml *F. columnare* B-30303 for 30 minute immersion exposure.
[2]Relative percent survival as determined by Amend (1981).

EXAMPLE 4

Fish were vaccinated (48 day post hatch channel catfish) with the modified live *F. columnare* B-30303 for two minutes at the described vaccine dose and then diluted with an equal volume of water and held for an additional 13 minutes (total vaccine time 15 minutes). Control and control non-challenged groups were immersed in vaccine diluent for the same duration of exposure (15 minutes). The fish were challenged 57 days following vaccination by co-habitation following 14 days without feed (Klesius et al., 1999). Three channel catfish showing signs of columnaris disease were added to each of the groups A, B and C and allowed to remain with fish for 24 hours. A sub-sample of five dead fish of those used for cohabitation were culture positive for *F. columnare*. The dead fish were removed at 24 hours the following day and feeding resumed. Table 3 shows the relative percent survival was calculated according to Amend (1981).

TABLE 3

PROTECTION AGAINST COLUMNARIS DISEASE AFTER IMMERSION VACCINATION OF CHANNEL CATFISH WITH *FLAVOBACTERIUM COLUMNARE* B-30303 VACCINE

| Group | Treatment | No. Dead/ No. Total | Mean % Mortality (SEM[1]) | Relative Percent Survival[2] |
|---|---|---|---|---|
| A | Vaccinated $1 \times 10^6$ CFU/ml | 2/150 | 1.33 (0.67)[a] | 96.4 |
| B | Vaccinated $5 \times 10^6$ CFU/ml | 7/150 | 4.67 (0.67)[a] | 87.3 |
| C | Control | 55/150 | 36.67 (17.7)[b] | — |
| D | Control Non-challenged | 3/150 | 2.00 (1.15)[a] | — |

[1]Means with different superscripts are significantly different at $p < 0.05$ using Duncan's Multiple range test for differences (SAS Inc., 1997).
[2]Relative percent survival calculated according to Amend (1981).

EXAMPLE 5

*Flavobacterium columnare* isolates were obtained from channel catfish with signs of columnaris disease. The *F. columnare* were cultured on *Cytophaga* agar and determined to be pure cultures. Isolates obtained were frozen in 2 ml aliquots at −80° C. Once thawed to 25° C., fifty microliters were then plated onto each of the media types (i.e., *Cytophaga* agar and *Cytophaga* agar supplemented with 5 µg rifampicin/ml) and incubated at 25±3° C. for 24 hours. The development of yellow rhizoid colonies on agar was considered positive for growth. The ten *F. columnare* isolates tested grew on *Cytophaga* agar only with typical *F. columnare* colonies developing. Growth was not observed with any of the isolates tested on *Cytophaga* agar supplemented with 5 µg rifampicin/ml.

Culture was also attempted after the isolates recovered from cold storage had grown on the non-rifampicin supplemented plates for 48 hours. Single colonies of the recovered bacteria that were growing on *Cytophaga* agar supplemented with 5 µg rifampicin/ml demonstrating that these isolates were not viable candidates for development of modified live *F. columnare* vaccines because rifampicin resistance could not be induced in these native *F. columnare* isolates (see Table 4) These results support the unexpected nature of the success achieved in Example 1.

TABLE 4

Failure of ten *Flavobacterium columnare* isolates tested to grow on rifampicin supplemented Cytophaga agar (5 µg rifampicin/ml)

| Isolate Identification[1] | Growth on Cytophaga Agar | Growth on Cytophaga rifampicin supplemented agar (5 µg rifampicin/ml) |
|---|---|---|
| AUFAA-1[2] | Yes | No Growth |
| AUFAA-2 | Yes | No Growth |
| AUFAA-3 | Yes | No Growth |
| AUFAA-4 | Yes | No Growth |
| AUFAA-5 | Yes | No Growth |
| ALG-530[3] | Yes | No Growth |
| ALG-515 | Yes | No Growth |
| ALG-513 | Yes | No Growth |
| ALG-527 | Yes | No Growth |
| ALG-521 | Yes | No Growth |

[1]*Flavobacterium columnare* isolates all from channel catfish showing signs of columnaris disease.
[2]AUFAA = Auburn University Fisheries and Allied Aquaculture - Isolate Number.
[3]ALG = Alabama Fish Farming Center, Greensboro, AL - Case Number.

It is understood that the foregoing detailed description is given merely by way of illustration and that modification and variations may be made therein without departing from the spirit and scope of the invention.

We claim:

1. A method of providing protection for fish against infection by virulent strains of *Flavobacterium columnare* comprising administering to said fish a vaccine at a dosage which is protective against infection by virulent strains of *Flavobacterium columnare* said vaccine comprising a carrier and an attenuated strain of *Flavobacterium columnare* resistant to rifampicin selected from the group consisting of NRRL B-30303 and B-30304.

2. A method of claim 1 wherein said fish is catfish.

3. The method of claim 1 wherein said administering is by means of immersion of said fish in an aqueous medium containing said vaccine.

4. The method of claim 2 wherein said administering is by means of immersion of said fish in an aqueous medium containing said vaccine.

5. The method of claim 3 wherein said attenuated strain of *Flavobacterium columnare* is present in the aqueous medium at a concentration greater than or equal to about $1 \times 10^5$ CFU/ml.

6. The method of claim 4 wherein said attenuated strain of *Flavobacterium columnare* is present in the aqueous medium at a concentration greater than or equal to about $1 \times 10^5$ CFU/ml.

* * * * *